(12) United States Patent
Brada et al.

(10) Patent No.: US 11,624,697 B2
(45) Date of Patent: Apr. 11, 2023

(54) DEVICE FOR MEASURING HAIR PROPERTIES

(71) Applicant: KONINKLIJKE PHILIPS N.V., Eindhoven (NL)

(72) Inventors: Ype Bernardus Brada, Leeuwarden (NL); Marcel Schouten, Hoogezand (NL); Maurits Koenen, Drachten (NL); Nikolaj Vasiljevitsj Zjiroecha, Drachten (NL); Mark Johannes Lelieveld, Shatin (HK); Chuen Yu Cyrus Pang, Fanling (HK); Michel Van Es, Groningen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 412 days.

(21) Appl. No.: 16/647,972

(22) PCT Filed: Sep. 12, 2018

(86) PCT No.: PCT/EP2018/074558
§ 371 (c)(1),
(2) Date: Mar. 17, 2020

(87) PCT Pub. No.: WO2019/057575
PCT Pub. Date: Mar. 28, 2019

(65) Prior Publication Data
US 2020/0217779 A1  Jul. 9, 2020

(30) Foreign Application Priority Data

Sep. 20, 2017 (EP) .................................... 17192029

(51) Int. Cl.
*G01L 1/00* (2006.01)
*G01N 19/02* (2006.01)
(Continued)

(52) U.S. Cl.
CPC ............... *G01N 19/02* (2013.01); *A45D 1/04* (2013.01); *A45D 2/001* (2013.01); *A46B 9/023* (2013.01);
(Continued)

(58) Field of Classification Search
CPC ...... G01N 19/02; G01N 33/4833; A45D 1/04; A45D 2/001; A45D 2044/07; A46B 9/023;
(Continued)

(56) References Cited

U.S. PATENT DOCUMENTS 4,167,869 A     9/1979  Gikas
5,868,146 A *   2/1999  Henninger ............... A45D 1/04
                                                          132/232

(Continued)

FOREIGN PATENT DOCUMENTS

DE     2719482      11/1978
EP     1958531       8/2008
(Continued)

OTHER PUBLICATIONS

International Search Report and Written Opinion dated Feb. 15, 2019 for International Application No. PCT/EP2018/074558 Filed Sep. 12, 2018.
(Continued)

*Primary Examiner* — Max H Noori

(57) ABSTRACT

A device for measuring hair properties has a first part (I) and a second part (II) between which hair (H) is guided. The first part includes a measuring probe (MP), and the second part is arranged for deforming the hair against the measuring probe. While the device moves along the hair, the measuring probe experiences both a friction force resulting from the hair being guided along the measuring probe, and a deformation force resulting from hair deformation by the second (Continued)

part against the measuring probe. The second part includes a pressure element (PB, S) for pressing the hair against the measuring probe. In alternative embodiments, the second part comprises alignment elements (AE) at opposite sides of the measuring probe, and guidance elements (G) for mitigating an influence of an angle at which the device is applied to the hair to the friction force and/or the deformation force.

21 Claims, 9 Drawing Sheets

(51) Int. Cl.
  *A45D 1/04* (2006.01)
  *A45D 2/00* (2006.01)
  *A46B 9/02* (2006.01)
  *A46B 15/00* (2006.01)
  *G01L 1/22* (2006.01)
  *G01N 33/483* (2006.01)
  *A61B 5/00* (2006.01)
  *A45D 44/00* (2006.01)
  *G01L 5/00* (2006.01)

(52) U.S. Cl.
  CPC ........ *A46B 15/0002* (2013.01); *A61B 5/0053* (2013.01); *A61B 5/448* (2013.01); *A61B 5/6887* (2013.01); *G01L 1/22* (2013.01); *G01N 33/4833* (2013.01); *A45D 2044/007* (2013.01); *A46B 2200/104* (2013.01); *A61B 2562/0252* (2013.01); *G01L 5/0028* (2013.01)

(58) Field of Classification Search
  CPC ............ A46B 15/0002; A46B 2200/10; A61B 5/0053; A61B 5/448; A61B 5/688; A61B 252/22; G01L 1/22; G01L 5/0028
  See application file for complete search history.

(56) References Cited

U.S. PATENT DOCUMENTS

| | | | |
|---|---|---|---|
| 6,817,222 | B2 | 11/2004 | Woolston |
| 9,808,061 | B2 * | 11/2017 | Ford .................. A45D 1/04 |
| 10,912,363 | B1 * | 2/2021 | Kanter ............... A45D 19/012 |
| 2009/0071228 | A1 | 3/2009 | Sherman |
| 2010/0147323 | A1 | 6/2010 | Hafemann |
| 2012/0024311 | A1 | 2/2012 | Linglin |
| 2015/0027486 | A1 * | 1/2015 | Lund .................. A45D 2/40 132/225 |
| 2015/0224655 | A1 * | 8/2015 | Talavera .............. B26B 19/20 30/179 |
| 2015/0342515 | A1 | 12/2015 | Hutchings |
| 2016/0022022 | A1 | 1/2016 | Lorenzi |
| 2016/0286928 | A1 * | 10/2016 | Weatherly ............ A45D 2/001 |
| 2017/0013929 | A1 * | 1/2017 | David .................. A45D 2/001 |
| 2018/0020795 | A1 * | 1/2018 | Keong ................. A45D 7/02 132/211 |
| 2018/0310692 | A1 * | 11/2018 | Knuebel .............. G06K 9/6282 |
| 2021/0022468 | A1 * | 1/2021 | Debenedictis ......... A45D 2/44 |
| 2022/0202159 | A1 * | 6/2022 | Lelieveld ............. A45D 2/001 |

FOREIGN PATENT DOCUMENTS

| | | |
|---|---|---|
| FR | 2442607 | 6/1980 |
| JP | S62280636 | 12/1987 |
| JP | 2006158526 A | 6/2006 |
| JP | 2007252657 A | 10/2007 |
| JP | 2012239615 A | 12/2012 |
| JP | 2019131896 A | 8/2019 |
| RU | 2605062 C2 | 12/2016 |
| WO | 2010027718 | 3/2010 |
| WO | 2011/064166 | 6/2011 |
| WO | 2011161381 | 12/2011 |
| WO | 2016014735 | 1/2016 |
| WO | 2018/114717 | 6/2018 |

OTHER PUBLICATIONS

Written Opinion of the International Preliminary Examining Authority dated Aug. 27, 201S for International Application No. PCT/EP2018/074558 Filed Sep. 12, 2018.
International Preliminary Report on Patentability dated Jan. 15, 2020 for International Application No. PCT/EP2018/074558 Filed Sep. 12, 2018.
ProDERM, "Suppleness of Hair by Pulling Force Determination" Jan. 2, 2017 http://www.proderm.de/de/proderm-kosmetik/markets/haarpflege/hair-suppleness.html.
ProDERM, "Friction Forces for Roughness of Hair Surface" Jan. 2, 2017 http://www.proderm.de/de/proderm-kosmetik/markets/haarpflege/friction-forces.html.
ProDERM, "Single, Hysteresis and Elastic Bending Forces" Jan. 2, 2017 http://www.proderm.de/de/proderm-kosmetik/markets/haarpflege/bending-forces.html.
Gupta, "Simple Method for Measuring the Friction Coefficient of Thin Fibers", J. Am Ceram. Soc, 74 171 1692-94 (1991).
Brandstetter, et al: "Effect of surface roughness on friction in fibre-bundle pull-out tests", Composites Science and Technology 65 (2005) 981-988.

* cited by examiner

DEVICE FOR MEASURING HAIR PROPERTIES

CROSS REFERENCE TO RELATED APPLICATIONS

This application is the U.S. National Phase application under 35 U.S.C. § 371 of International Application No. PCT/EP2018/074558 filed Sep. 12, 2018, published as WO 2019/057575 on Mar. 28, 2019, which claims the benefit of European Patent Application Number 17192029.1 filed Sep. 20, 2017. These applications are hereby incorporated by reference herein.

FIELD OF THE INVENTION

The invention relates to a device for measuring hair properties.

BACKGROUND OF THE INVENTION

US 2009/0071228 A1 discloses a method for measuring the surface smoothness of hair, by using a handheld friction sensor comprising a clamping member and a load cell. A key indicator of the overall condition of hair is friction. Load cells are well known in the art for measuring friction, and can be readily incorporated into a variety of devices. A bundle of hair is placed between the clamping member and the load cell, and the clamping member is closed, which creates a substantially constant normal force against the hair sample and load cell. The device is pulled across the bundle of hair at a substantially constant rate in the root to tip direction of the bundle of hair, and the coefficient of friction of the material creates a voltage in the load cell, which is correlated to a hair smoothness value based upon the measured coefficient of friction.

DE 2719482 A1 discloses a specialized hairdresser's comb, which incorporates a strain gauge that can be used quantitatively to assess the effectiveness of various kinds of hair treatment by measuring the resistance of hair to combing before and after treatment. A steel comb has a strain gauge mounted roughly between teeth and handle, with a cable and plug attachment. When the hair is combed, a reading is obtained from the circuit associated with the strain gauge of the deflection of the comb and so of the resistance to combing of the hair.

FR2442607 A1 discloses a flexible plastic comb that has a metallic plate riveted to it and which supports a sensor comprising four strain gauges connected in a bridge arrangement. The bridge is powered from a battery connected across one of its diagonals. A cable allows the battery to be located at the counter circuit and also allows the bridge output to be applied to a voltage to frequency converter. The output is applied to a pulse counter with a numerical readout. The counter reading is proportional to the force required to untangle the hair. This arrangement allows the relative characteristics of different shampoos to be compared.

U.S. Pat. No. 4,167,869 A discloses an apparatus for measuring the incremental grooming force experienced by a hair tress during combing, and supplying an instantaneous readout of that force. The apparatus includes a comb or brush with strain gauges attached to it which change resistance when mechanically deformed. The change in resistance is electrically measured to provide an indication of incremental grooming force. A continuous monitor is connected to the resulting electrical signal to provide an instantaneous indication of incremental grooming force.

US2010147323 A1 discloses a hair styling device having two arms. Each arm has a styling part, which cooperates with the styling part on the other arm for the hair styling operation. At least one styling part is designed for heating hair inserted into the hair styling gap located between the styling parts. A pressure measuring device is included in one of the two arms. The pressure measuring device detects the pressure, or a value representing this pressure, exerted on the hair between the styling parts when the hair styling gap is closed. The hair styling device also has a display device for displaying the pressure or pressure value thus detected.

EP1958531 A1 discloses an ultrasonic wave hair set apparatus comprising a main frame, an ultrasonic vibration generating means which is provided on the main frame and generates ultrasonic vibrations, and a burn injury prevention means that prevents a portion of a human body other than hairs from touching the vibration face of the ultrasonic wave generating means. An embodiment further comprises a pressing means having a pressing face which presses hairs to a vibration face, a pressure detection sensor which detects a pressure applied to the pressing face, and a driving circuit which drives the ultrasonic vibration generating means to generate ultrasonic vibrations only when a pressure detected by the pressure detection sensor becomes equal to or larger than a predetermined pressure.

SUMMARY OF THE INVENTION

It is, inter alia, an object of the invention to provide an improved device for measuring hair properties. The invention is defined by the independent claims. Advantageous embodiments are defined in the dependent claims.

Embodiments of the invention provide a device for measuring hair properties. The device has a first part and a second part between which hair is guided. The first part comprises a measuring probe, and the second part is arranged for deforming (e.g. squeezing, bending) the hair against the measuring probe. While the device moves along the hair, the measuring probe experiences both a friction force resulting from the hair being guided along the measuring probe, and a deformation force resulting from the hair being deformed by the second part against the measuring probe.

The second part may comprise a pressure element for pressing the hair against the measuring probe, to squeeze the hair. Preferably, this squeezing results from pushing the pressure element into the direction of the measurement probe while the hair is being guided between the pressure element and the measuring probe, while the hair is not squeezed before the hair is being guided between the pressure element and the measuring probe. One of the pressure element and the measuring probe may comprise a pin, while another one of the pressure element and the measuring probe is provided with a hole for receiving the pin. A spacer may be applied between the first part and the second part so as to provide a minimum gap between the measuring probe and the pressure element. The minimum gap may have a width of about 0.2 mm.

In alternative embodiments, the second part comprises alignment elements at opposite sides of the measuring probe for bending the hair against the measurement probe, and guidance elements for mitigating an influence of an angle at which the device is applied to the hair to the friction force and/or the deformation force, while the measuring probe is mounted to a load cell module for measuring a load in two dimensions to measure friction force and deformation force, respectively.

The hair measurement may be embedded in a hair styling device having a treatment plate. If so, the measuring probe is preferably positioned along the treatment plate, and advantageously, a length of the measuring probe substantially matches a length of the treatment plate.

Preferably, the measuring device further comprises an arrangement to compensate for a weight of the measurement probe. The arrangement advantageously includes an accelerometer for measuring gravity in a measurement direction of the measurement probe.

These and other aspects of the invention will be apparent from and elucidated with reference to the embodiments described hereinafter.

DESCRIPTION OF EMBODIMENTS

There is a wish in the haircare domain to analyze and assess hair condition and/or hair health. Women tend to judge their own hair by touching and combing their hair with their fingers. One embodiment provides a product where the principle of determining "hair feel", i.e. a combination of surface roughness of the hair and the ease to deform a tress of hair, is measured in a separate analyzer outside of a laboratory environment and translated into an indication of hair health.

A first group of embodiments of the invention enable determination and quantification of hair characteristics by measuring a combination of surface friction force and squeeziness (squeezing a bundle of hair) of a tress of hair with a single sensor. The combination of friction and squeeziness is closely related to the way the human finger assesses hair. The sensor may include a measuring probe (e.g. a load cell, e.g. shaped as a cylinder) and a counterpart pressing a hair tress with a constant force to the measuring probe. By pulling the hair tress between the measuring probe and the pressure bar, the reaction force is measured by the load cell. By filtering and processing the measured values, hair characteristics are derived. The device quantifies the "hairfeel" by measuring a combination of surface friction and squeeziness while being small enough to be built into a hair styling device or other handheld device, and does not need special handling to operate and goes in one flow with the styling process. The best description of "hair feel" is a combination of surface roughness of the hair and the ease to deform a bundle of hair (squeeziness). For that, an embodiment of the measuring device comprises the following key features:

Measuring a combination of friction and tress deformation with just two contact elements.

Entrapping a hair tress by just an open and close action.

One sensor measuring a combination of friction and deformation, where the ratio of the contribution of friction and deformation force can be controlled by changing the geometrical aspects of the two contact elements. One of the contacting elements also is used to measure the force (e.g. by a measuring probe).

In an embodiment, the sensor is built into a styling device like a hair straightener, but the sensor can alternatively be incorporated in other devices having an open/close functionality, or in a stand-alone device.

Figure 1:
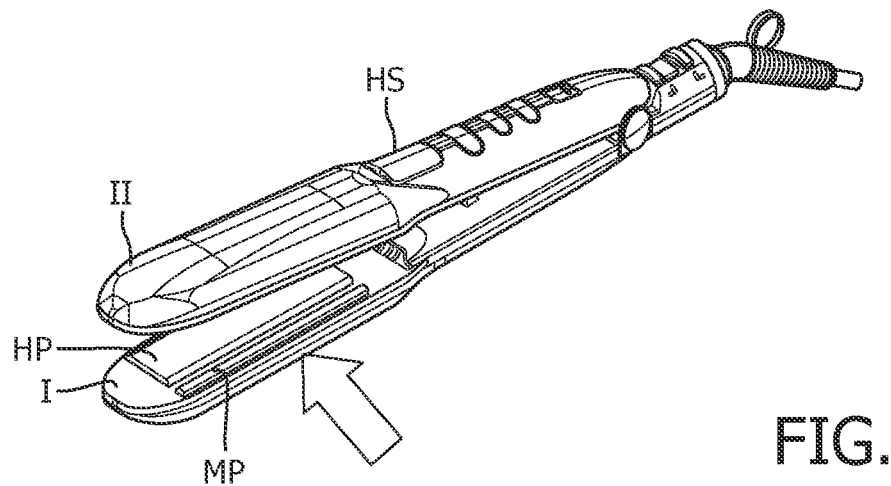
FIG. 1 shows an embodiment of a device for measuring hair properties embedded in a hair styling device.

FIG. 1 shows an embodiment of a device for measuring hair properties embedded in a hair styling device HS having a treatment plate HP. The treatment plate HP may be a conventional heating plate of a hair iron, or a transparent plate in case optical radiation is applied to the hair to style the hair. Alongside the treatment plate HP on the lower leg I of the hair styling device HS, there is a measuring probe MP. The arrow in FIG. 1A shows the movement direction of hair.

Figure 2:
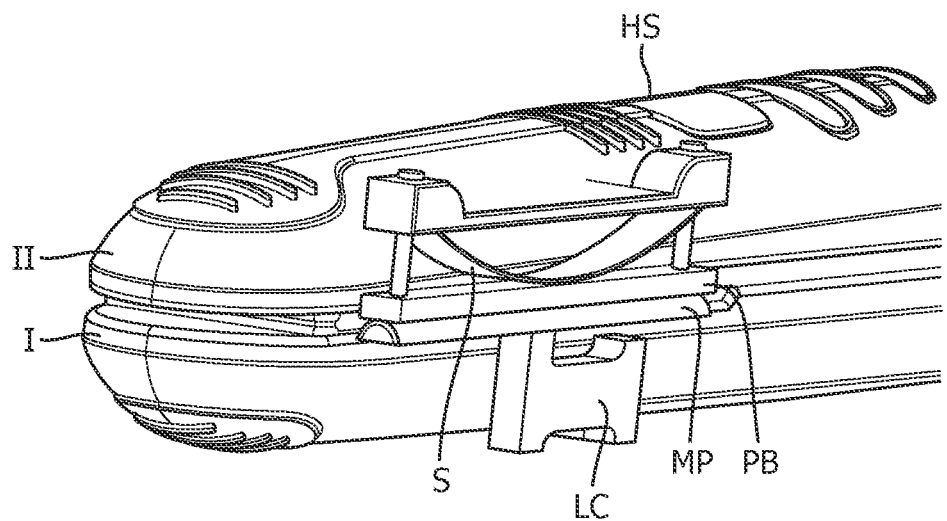
FIG. 2 illustrates an embodiment of a first way to implement the invention.

FIG. 2 illustrates an embodiment of a first way to implement the invention. In the embodiment of FIG. 2, inside the upper leg II of the hair styler HS there is a pressure element formed by a pressure bar PB pushed downwards by a spring S. Inside the lower leg I of the hair styler HS, below the measuring probe MP, there is a load cell LC.

The embodiment of FIG. 2 has the following 4 key components:

Measuring probe MP: cylindrical element (but not necessarily cylindrical) with a certain diameter (e.g. 5 mm, but not limited to that dimension), a certain length (e.g. 90 mm, but can be any length of at least 5 mm), and a certain roughness. Roughness is very important parameter for the result of the measurement, but is preferably low because of least influence by pollution. Roughness and cylinder diameter will influence the ratio of the contribution of surface friction and deformation force. Preferably, if the measuring probe MP is embedded in a hair straightener HS, the length of the measuring probe MP equals that of the treatment plate HP to prevent hairs from being too easily squeezed out of the measuring system. Because of the length of the measuring probe MP, a momentum is created on the load cell LC measuring the friction and deformation (e.g. squeezing) force, resulting in a sensor signal that is depending on the location where the hair tress H touches the measuring probe MP. This problem can be simply overcome by the application of a parallel hinge structure, also seen in load cells applied in weighing scales.

Load cell LC: in an embodiment this may be a standard shear type strain gauge sensor with maximum load of 1 N. It is mounted in such way to the measuring probe MP that the measurement direction is perpendicular to the clamping direction. The sensor is not limited to this type of sensor, but can be a force measuring system of any kind. For example, a piezo load cell may be used.

Pressure bar PB: this element forces a hair tress rubbing against the probe, enabling measuring reaction forces. In the example, the element has a flat surface, but the geometry is largely influencing the ratio of the contribution of surface friction and deformation force.

Pressure spring S: This element presses the pressure bar PB with a defined force against the measuring probe MP when the device is closed. So when a hair tress is in-between the pressure bar PB and the measuring probe MP, the hair is squeezed with a defined force. In an example, the pretension of the spring is 0.75 N. A lower force will result in a lower signal amplitude. A higher force will result in a better signal, but also in more pulling on the hair on the head. The force also influences the ratio between friction and deformation force.

Figure 3:
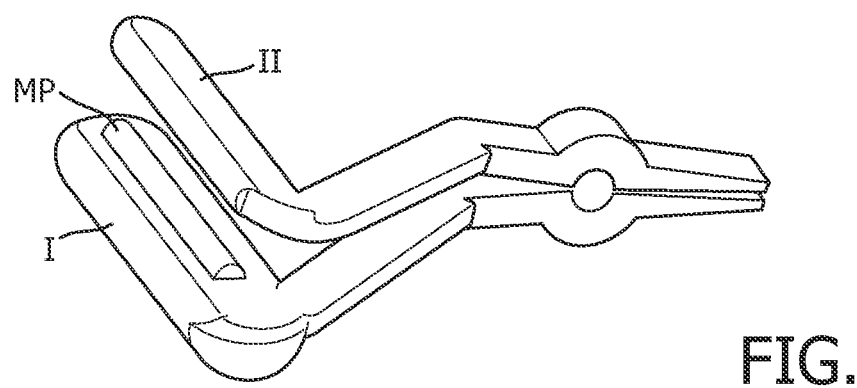
FIG. 3 shows an embodiment of a stand-alone device for measuring hair properties.

FIG. 3 shows an embodiment of a stand-alone device for measuring hair properties. While FIG. 3 only shows the measuring probe MP, in the upper half II of the device, there is a pressure bar PB pushed downwards by a spring S, and in the lower half I of the device, attached to the measuring probe MP there is a load cell LC, just like in FIG. 2.

Figure 4A:
FIGS. 4A-4D illustrate the principles of embodiments of the first way to implement the present invention.
Figure 4B:
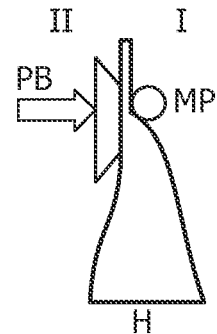
Figure 4C:
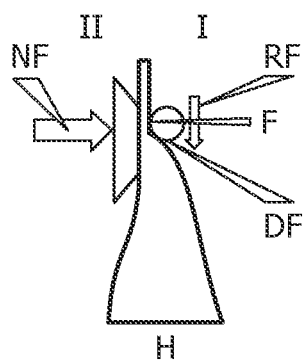

FIGS. 4A-4D illustrate principles of embodiments of the present invention belonging to the first group of embodiments. FIG. 4A shows a hair tress H, falling from the head of a person. FIG. 4B shows that on one side, the measuring probe MP is placed against the hair tress H. When the hair styling device HS is closed, the pressure bar PB is pressed to the opposite side of the measuring probe MP, with the hair tress H trapped in-between. The pressure spring S guarantees a constant force. The hair tress H is pulled through the system by moving the device in a downward direction. As illustrated in FIG. 4C, two things happen on the reaction force RF on the sensor (measurement direction according the arrow in the picture):

Due to the normal force NF of the pressure bar PB, on the opposite side on the measuring probe MP, a pure surface friction F of the hair tress H will be measured.

Due to the squeezing effect, resulting in a deformation force DF, the hair tress H will push against the lower part of the measuring probe MP, causing the reaction force RF. The amplitude of this force depends to a large extent on the ease of the squeezing of the hair tress H, and thus on the properties of the hair.

Figure 4D:
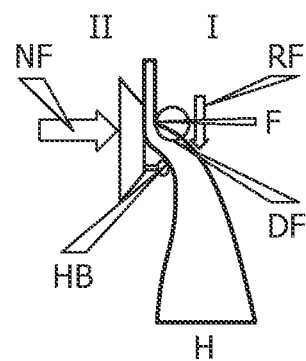

FIG. 4D shows an example on how to change the ratio between surface friction and the deformation force DF. A hair bending element HB on the pressure bar PB is forcing the hair tress H to make it harder to squeeze, causing a larger reaction force to the lower part of the measuring probe MP. Many different executions can however be thought of.

Figure 5:
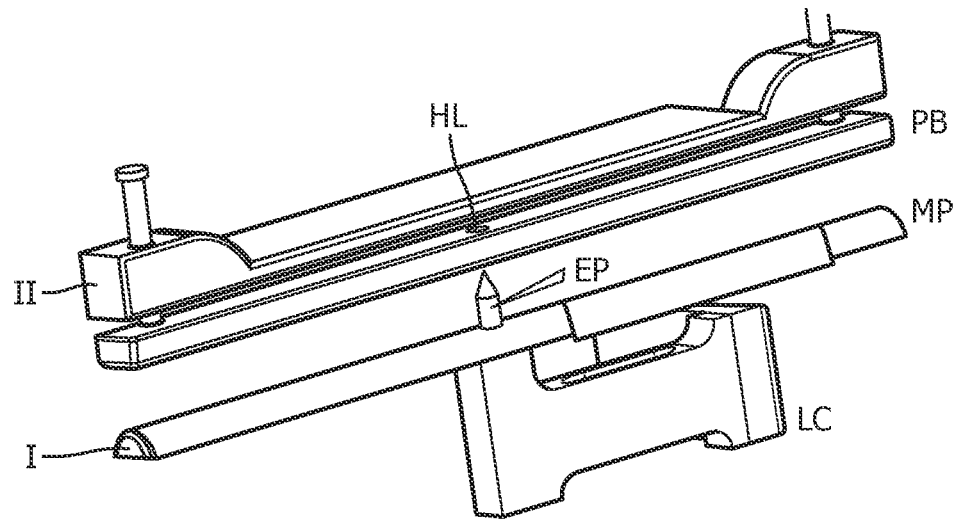
FIG. 5 shows a second embodiment of a device for measuring hair properties according to the first way to implement the invention.

An important aspect in hair characteristics is the level of entanglement of the hair tress. Based on surface friction and deformation alone, it is hard to determine this entanglement. Because of that, in the embodiment of FIG. 5, a pin EP is mounted on the measuring probe MP, and a hole HL is made in the pressure bar PB. By a kind of combing action, it can be determined if hair tresses are entangled. One execution is as shown, another execution is one where the pin can easily be mounted and dismounted.

Figure 6:
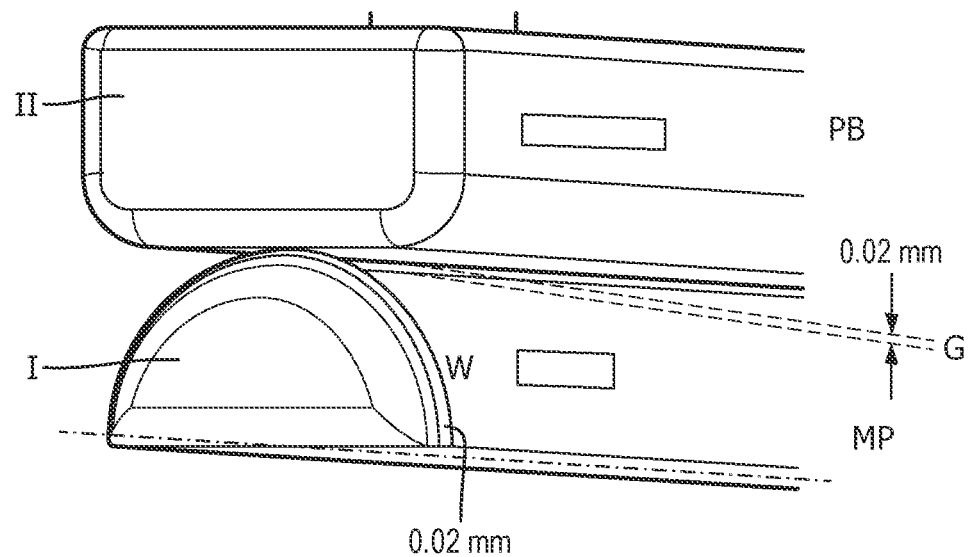
FIG. 6 shows a third embodiment of a device for measuring hair properties according to the first way to implement the invention.

Although the results of the above measuring system are satisfying, the signal may be polluted by pulling on a few hairs. As long as sufficient hairs are present between measuring probe MP and pressure bar PB, the contact pressure is relative low. When just a few hairs are in the system, and this happens often at the ultimate tip of a tress, the pressure increases enormously resulting in a deformation of the hair (Hertz contact pressure), resulting in clamping. Not only the output of the sensor is polluted by a non-realistic value but also a painful sensation is felt on the user's head. To that end, in the embodiment of FIG. 6, a spacer is applied between the first part I and the second part II so as to provide a guaranteed gap between the measuring probe MP and the pressure bar PB. It suffices to provide a guaranteed opening between the measuring probe MP and the pressure bar PB of about 0.2 mm. This size is based on the maximum thickness of a hair. To minimize the chance of trapping a hair, the element to create the gap should be narrow. A possible way to meet this both requirements is applying a wire with diameter 0.2 mm around the pressure bar PB or the measuring probe MP. In another execution, narrow elements with a height of about 0.2 mm can be fixed to the measuring probe MP or the pressure bar PB. In the embodiment of FIG. 6, a 0.2 mm thick wire W is provided on the measuring probe MP to provide a gap G of 0.2 mm. In yet another execution, the narrow elements can be embossed in the measuring probe MP or the pressure bar PB. The width of the spacer is limited by the fact that the high pressure of the spacer to the opposite element should not exceed the maximum allowable contact pressure.

The above embodiments of the invention enable determination and quantification of hair characteristics by measuring a combination of surface friction force and squeeziness of a tress of hair with a single sensor. The sensor is meant to be used in a non-controlled user environment and should be able to measure small differences in forces on the hair. A preferred embodiment of the invention is based on the recognition that the changing orientation of the device, due to the user operating the device, may cause a significant error caused by the weight of the measuring probe. By measuring the contribution of the weight in the direction of the measurement direction, the effect of the weight of the measuring probe can be compensated. An advantageous embodiment provides a compensation of the weight by using a 1-directional accelerometer.

A hair styler may be used in all possible orientations. The friction and deformation force is measured with a measuring probe having a certain weight. In an embodiment, this weight is added to the friction signal, depending on the orientation of the styler and based on the direction of the gravity vector. Because the weight of the measuring probe may be substantial in the signal, the contribution of the weight is advantageously eliminated from the force sensor readings. A main element of this embodiment is to know the momentary contribution of the weight of the measuring probe to the signal of the deformation force sensor. To that end, the embodiment uses:

- a 1-directional absolute accelerometer positioned in the direction along the measurement direction (or another 1-directional sensor determining the contribution of the gravity in the measurement direction of the deformation force sensor), and
- the known weight of the measuring probe.

The resulting output is not influenced by the weight:

Friction and deformation force [N]=Sensor output [N]−(Accelerometer output [m/s$^2$]*Weight [g])

In an embodiment, the compensation involves:

A sensor measuring the gravity in the same direction as the direction of the deformation force sensor. In the example it is performed with a standard accelerometer, such as accelerometers that are used in smartphones. Another execution may be a second force sensor, with a certain mass positioned in the same direction as the deformation force sensor with the measuring probe. The second force sensor is able to measure the contribution of the gravity to the measurement signal. In practice, to meet the requirement of measuring in the same direction of both systems, the deformation force sensor and the accelerometer are mounted to the same structure in the measuring device.

The knowledge of the weight of the measuring probe.

Most likely (but not necessarily) a microcontroller, subtracting the accelerometer compensation data from the deformation force sensor signal to obtain the "real" force signal. Another execution might be an analog subtraction circuit when an analog sensor is used to derive the gravity contribution. It is even possible to have no circuit at all when the same sensor is used for force sensing and gravity sensing with a mass attached to the gravity sensor equal to the mass of the measuring probe. In this case, the signals can be directly subtracted from each other resulting in the compensated force signal.

If due to handling of the device by the user, the orientation of the deformation force sensor has an angle φ to z-axis of the world coordinate system, where the z-axis is in the negative direction of earth's gravity, the output of the force sensor during use will be:

Force sensor output=Friction force+Weight*$g \cos(\varphi)$

Because the orientation of the accelerometer is mechanically coupled to the orientation of the deformation force sensor, at the same time the output of the accelerometer will be:

Accelerometer output=$g \cos(\varphi)$

Together with the known weight of the measuring probe, the microcontroller can calculate the compensation by multiplying the accelerometer output with this known weight:

$$\text{Calculated compensation} = \text{Weight} * \text{Accelerometer output}$$
$$= \text{Weight} * g\cos(\varphi)$$

If when the deformation force is measured, the compensation is added to the signal, only the required friction force is determined by the measurement system:

$$\text{System output} = \text{deformation force sensor output} -$$
$$\text{Calculated compensation}$$
$$= \text{Friction force} + \text{Weight} * g\cos(\varphi) - (\text{Weight} * g\cos(\varphi))$$
$$= \text{Friction force}$$

To ensure that the contribution of acceleration due to movements is low compared to gravity, the weight of the measuring probe is preferably as low as possible.

A second way to implement the present invention provides a hair health analyzer enabling determination and quantification of hair characteristics by determining a relative friction coefficient using two sensors, which can again be implemented as load cells. The basic principle for an embodiment of the second way to implement the invention is to use the bending stiffness of hair to apply a deformation force formed by a normal force to a surface to measure a dynamic friction coefficient of a hair tress and along the length of a hair tress. One sensor (load cell LC-Y in the Y direction) measures surface friction force between hair and a measuring probe, and the other sensor (load cell LC-X in the X direction) measures a dynamic bending stiffness of a tress of hair (which is the normal force applied on the measuring probe surface). The sensor combination is built into a hair analyzing device, or in a hair styling device e.g. as shown in FIG. 1. Using the hair health analyzer, a tress of hair is clamped between two pins and the measuring probe, and the hair health analyzer is pulled from tip to root. A relative friction coefficient may be calculated by a hair health algorithm, using the output of the two sensors.

An embodiment of the device quantifies the "hair feel" by determining the friction coefficient using the output of a two sensor combination. Simultaneously, the sensors measure two forces, a force related to the motion of two surfaces upon each other, and a force perpendicular to the pulling axis, so friction and normal force, respectively. The normal force is generated by forcing the hair to be bent over the measuring probe. While being small enough to be built in into a separate analyzer, both sensor outputs are used to determine the friction coefficient over time, which limits the need for special handling to operate and can easily be used by a consumer and outside a controlled laboratory environment.

An embodiment provides a measuring device where friction force and deformation force (here: bending force) of hair are determined with the following key features:

Using a 3-point bending stiffness test set-up for:
Tress deformation measurement by measuring the deformation force (here: bending force) perpendicular to the tress pull direction.
Applying a normal force to the sensor surface to detect friction using the bending force of the hair.

Entrapping a tress by just an open and close action.

Figure 7:
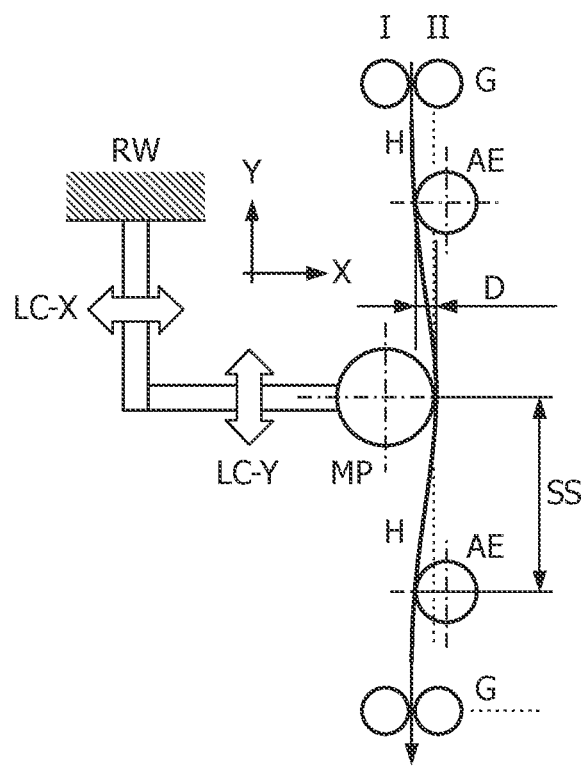
FIG. 7 shows an embodiment of an embodiment of a second way to implement the invention.

Measuring simultaneously the dynamic bending force (X direction) and friction force (Y direction) along the length of a hair tress using two sensors, while the ratio between friction and bending force can be optimized by changing the geometrical aspects of the three elements of the test system, viz. two supports and one measuring probe (see FIG. 7 for a measuring device configuration). Using both sensors, a dynamic relative friction coefficient along the hair tress can be determined.

An embodiment as shown in FIG. 7 comprises four key components:

1. Measuring Probe MP: Cylindrical element (but not necessarily cylindrical) with a certain diameter (here 6 mm, but not limited to that dimension), a certain length (here 12 mm, but can be any length) and certain roughness (here Ra of ~0.3, but can be of any surface roughness). Friction between two surfaces is a function of surface roughness and contact surface area. Roughness and surface contact area are expected to influence the ratio of the friction coefficient, caused by an increase or decrease in surface friction.

Figure 8:
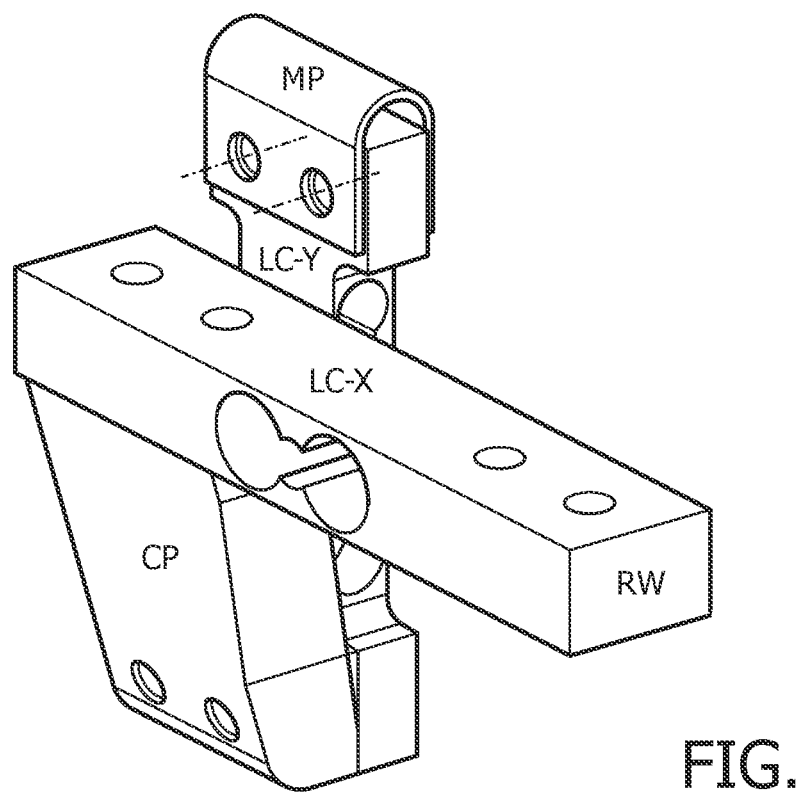
FIG. 8 shows a load cell module for use in the embodiment of FIG. 7.

2. Load cell module (see FIG. 8 for more details): In this case standard shear type strain gauge sensors with maximum load of 1 N (Y-direction) and 7.8 N (X-direction). They are mounted in such a configuration that both sensors are measuring in the intended direction without influencing each other. The sensors are not limited to this type of sensor, but can be a force measuring system of any kind. The load cell module comprises a first load cell LC-Y in the Y direction connected to the measuring probe MP, a connection piece CP, and a second load cell LC-X in the X direction. The second load cell LC-X has a surface RW that is connected to the real world.

3. Alignment elements AE formed by supports (e.g. support pins) are positioned alongside (at support spans SS of e.g.

6.35 mm in an embodiment in which the measuring probe radius is 2.7 mm) the measuring probe MP with a constant overlap, length, diameter and material, in this case with an overlap or deflection D of 4 mm, a length of 20 mm, a diameter of 4 mm, and stainless steel as material, but can be of any dimension, length, diameter and material. The overlap D determines the contribution of the force in X direction (normal force) of the friction coefficient, which is a function of hair tress volume and individual hair bending stiffness. The alignment elements AE may be static, but can be dynamic by using rollers to decrease pull force or incorporate a velocity sensor. The alignment elements AE are used to bend the hair H and use the hair flexible stiffness to apply a normal force on the measuring probe MP. The radius of the curvature can be adjusted by moving the alignment elements (support pins) AE towards the measuring probe MP (deflection) or move it in the X direction (support span SS). Differences in X and Y direction will increase or decrease the normal force to the system.

4. Guidance elements G formed by elements to contribute to the elimination of pull forces in the system, caused by the hold angle. These elements have a certain diameter and material (here 4 mm and stainless steel), but can be of any diameter and material. The guidance elements G may be static, but can be dynamic by using rollers to decrease pull force or incorporate a velocity sensor.

In the embodiment of FIG. 7, the left guidance elements G, the measuring probe MP and the load cell module belong to one part I of the device, while the right guidance elements G and the alignment elements AE belong to another part II of the device, between which the hair H is guided. The alignment elements AE and guidance elements G absorb the pulling forces required to remove additional forces from the sensor system, ensuring a clean friction measurement in Y direction, which is independent of velocity. The tip parts (distally) of the hair are free to move in all directions and the top (proximally) part of the hair is attached to the scalp.

The alignment elements AE and guidance elements G provide another advantage. With a hand-held device it is difficult to use same angle, velocity and volume of hair tress during measurements or per individual measurement. One of the factors is the angle of the incoming hair tress with respect to the device, which will change while using the device by an end user. The positioning of the guidance pins G and support pins AE provides an equal configuration between the hair tress H and the measuring probe MP for each measurement. By default, the chosen design ensures a constant angle at the area where the hair friction is measured. In particular, the guidance elements G will condition the hair to enter the test area with same angle, independent of the angle at which the user applies the device to the hair H. Through this configuration, the bending curvature of the hair is standardized independent of the user angle.

Figure 9A:
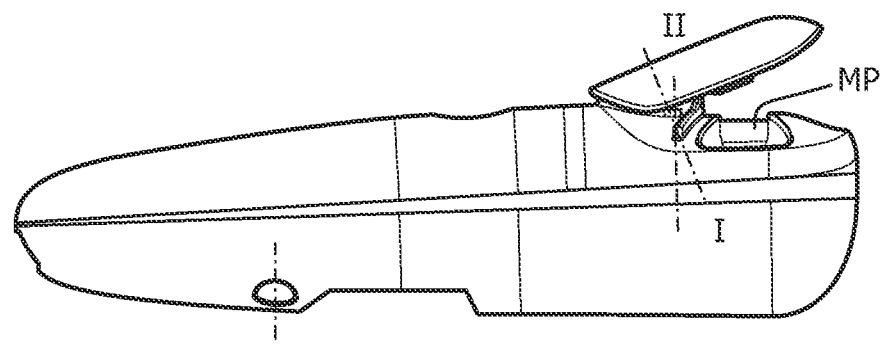
FIGS. 9A-9B show an embodiment of a standalone hair properties measuring device in accordance with the second way to implement the invention.
Figure 9B:
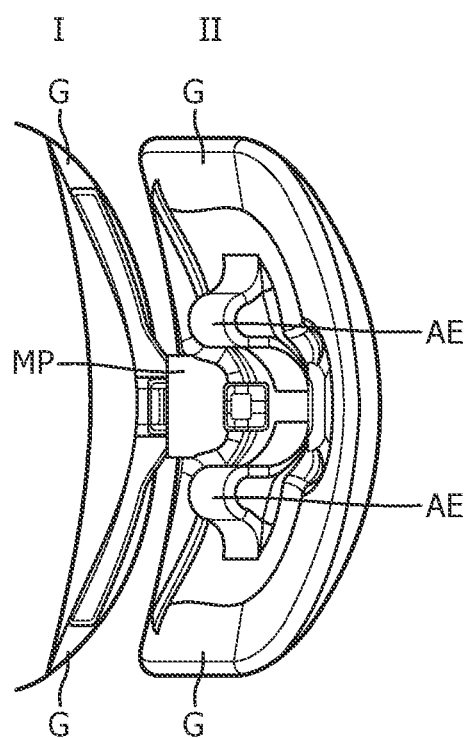

FIGS. 9A-9B show an embodiment of a standalone hair properties measuring device in accordance with the second way to implement the invention, with the measuring probe MP and half of the guidance elements G in the body part I, in which also the load cell module is located, and the alignment elements AE and the other half of the guidance elements G in the lid part II of the measuring device. The guidance elements G are preferably oriented such that the hair will enter flat and straight towards the measurement unit (supports and measuring probe MP), and to that end, they may have hinged surfaces.

In an embodiment, the measurement is carried out as follows:

1. The system is default open or closed prior to introduction of a hair tress H to the system, and can be opened or closed e.g. by pushing a button or in another suitable way.
2. Introduce the hair tress H to the system between a measuring probe MP and alignment elements (e.g. support bars) AE.
3. Close the system to clamp the hair tress H between the alignment elements (support bars) AE and the measuring probe MP. Guidance elements G have a small gap in between, of e.g. 2 mm (but can be of any gap size), determining the pull force of the analyzer by the user and amount of hair in the system.
4. Pull the analyzer downwards to the tip of the hair tress H. During downwards movement, the friction will be determined between the surface of the measuring probe MP and the hair tress H, and simultaneously the normal force is calculated over time or along the length of the hair tress. This is a function of the bending stiffness of the hair tress H between the alignment elements AE and the measuring probe MP.
5. The data of both sensors is received, whereafter a friction coefficient over time is determined using the following equation:

$$\mu_{Friction\ hair\ tress} = \frac{\left(\sum_{i=1}^{n} \frac{F_{Friction\ hair\ tress(i)}}{F_{flexural\ stiffness\ hair\ tress(i)}}\right)}{n}$$

Herein, the various notions have the following meanings:

| Symbol | Definition |
| --- | --- |
| $\mu_{Friction\ hair\ tress}$ | Friction coefficient of the total hair tress. |
| $F_{Friction\ hair\ tress}$ | Friction force measured |
| $F_{flexural\ stiffness\ hair\ tress}$ | Normal force measured (deformation force) |
| n | Amount of data samples recorded |

The friction coefficient is used as parameter to determine the "hair feel" of the user.

Figure 10A:
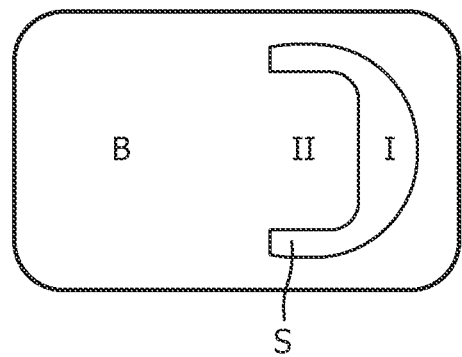
FIGS. 10A-10D illustrate an embodiment of a measuring device as part of a top side of a brush.
Figure 10B:
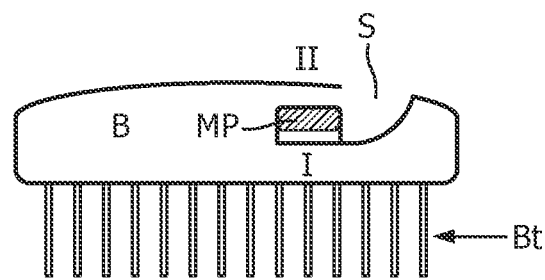
Figure 10C:
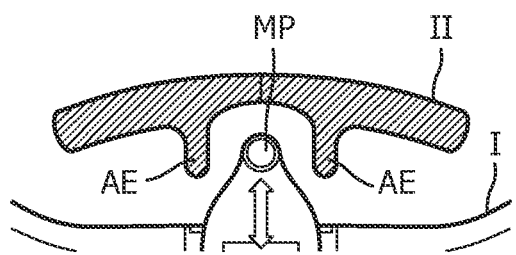
Figure 10D:
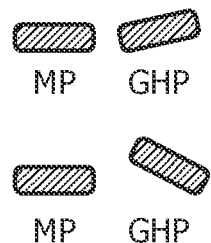

Advantageously, the thus calculated friction coefficient, based on both the friction force and the deformation force measured by respective load cells LC-X and LC-Y, is not influenced by volume changes as may e.g. result from damaged hair, or from the hair H having been cut in layers so that the volume of the hair tress is not constant over the length of the hair tress. If only the normal force or the friction force were measured, the result would be a system that is highly influenced by the amount of hair that a user puts into the system FIGS. 10A-10D show a brush with a sensing module in the back. The hair is manually inserted in a slot that contains the measuring probe. The measuring device can thus be part of the top side of a brush B, of which the bristles Bt are mounted at the bottom side. FIG. 10A shows the top of the brush B, FIG. 10B shows a cross-section along a horizontal line in the middle of FIG. 10A, FIG. 10C shows a cross-section along a vertical line in FIG. 10A through the reference sign II, and FIG. 10D shows some sketches of the measuring probe MP and a guidance and holding part GHP for use in this brush B.

As shown in FIGS. 10A and 10B, the top side of the brush B is provided with a slit S, in which the hair can be guided. The second part II of the measuring device of FIGS. 10A-10D is fixed, while in the embodiment of FIGS. 9A-9B it was hinged. The top of the second part II of the measuring device is at the same level as the top of the brush B, while the first part I of the measuring device is in a cavity in the top of the brush B. FIG. 10C shows a cross-section, having the same elements as discussed before: measuring probe MP and alignment elements AE. To allow the hair to easily enter the measuring device, it is possible that the measuring probe MP moves downwards when a lock of hair is entered, whereafter it moves upwards to ensure that the second part II deforms the hair H against the measuring probe MP while the hair H is guided between the first part I and the second part II. In an implementation, sketched in FIG. 10D, a guidance and holding part GHP, positioned before the measuring probe MP in the hair entrance direction, is in a down position when hair is entered (shown in the upper half of FIG. 10D), and in an up position preventing hair from escaping sideways (i.e. in a direction perpendicular to the hair H) while the hair is guided between the first part I and the second part II, as shown in the lower half of FIG. 10D.

Figure 11A:
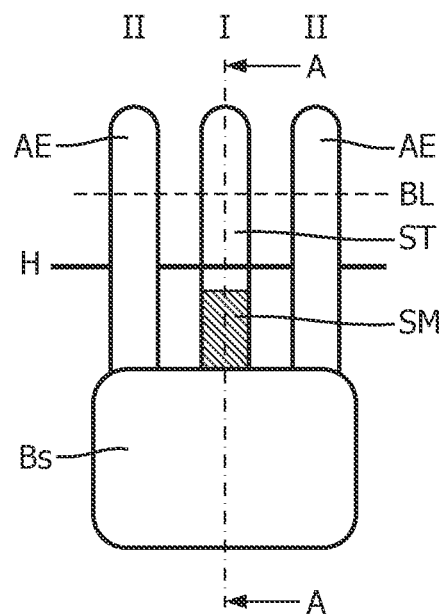
FIGS. 11A-11C show another embodiment of the measuring device of the present invention.
Figure 11B:
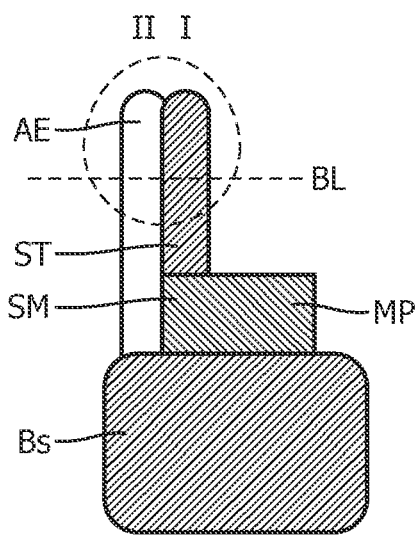
Figure 11C:
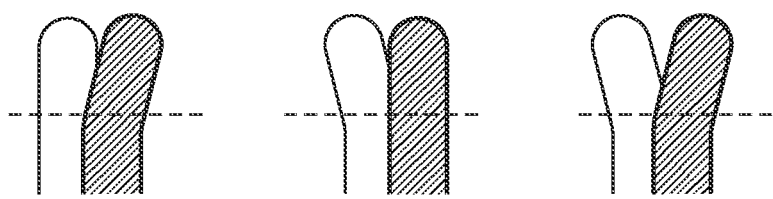

FIGS. 11A-11C show another embodiment of the measuring device of the present invention. FIG. 11A shows a front view, and FIG. 11B shows a cross section through line A-A in FIG. 11A. FIG. 11C shows three possible variations of the measuring probe MP and the alignment elements AE, as alternatives to the encircled part of FIG. 11B. The measuring device of FIGS. 11A-11C has a base Bs on top of which three teeth are placed, which form the two alignment elements AE and the measuring probe MP, respectively. The measuring probe MP comprises a sensor module SM on top of which a sensor tooth ST is placed. The sensor module SM may be positioned inside the base Bs. The teeth AE, ST can be either fully solid, or flexible above a bend line BL to prevent excessive hair pulling from occurring if the hair is tangled. Like the embodiment of FIGS. 10A-10D, the embodiment of FIGS. 11A-11C has no moving parts I and II.

As shown in FIG. 11C, the alignment elements AE and/or the sensor tooth ST preferably have tilted tips above the bend line BL to facilitate hair insertion into the measuring device. To ensure that while the device moves through the hair, the hair does not escape the device at the top (i.e. in a direction perpendicular to the hair H), the alignment elements AE and/or the sensor tooth ST may be provided with a hair blocking element (not shown) positioned at about the bend line BL, which hair blocking element is manually or automatically operated. This hair blocking element may also serve to block hair from entering further once a defined amount of hair has entered the sensing area. This hair blocking element can, for example, be actuated once the force sensor is above a certain threshold and deactivated if the sensor output appears stable.

FIGS. 12A-12E show embodiments of a brush B having a measuring device at the side where the bristles Bt are located. The device has the same elements as discussed with previous embodiments: measuring probe MP, alignment elements AE, and guidance elements G. Like in FIGS. 10A-10D and 11A-11C, the first part I and second part II are mounted in a fixed relation; the various elements can be allocated to the first part I and the second part II like in the embodiment of FIG. 7.

Figure 12A:
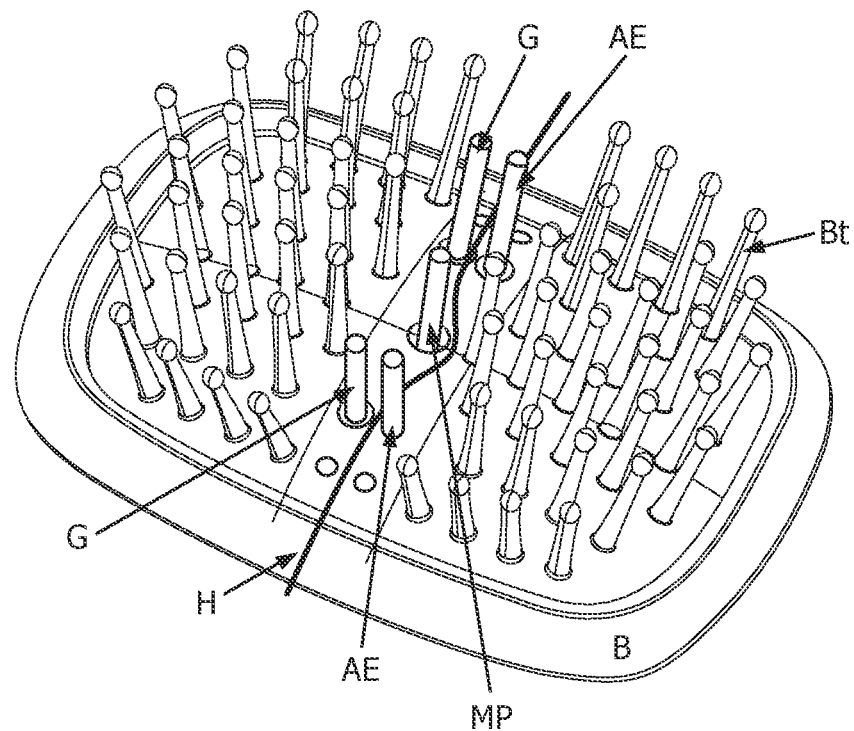
FIGS. 12A-12E show embodiments of a brush having a measuring device at a side where bristles are located.

The embodiment of FIG. 12A is based on the measuring device of FIG. 7. The basic execution is in such way, that while brushing the hair, the hair H is guided along the alignment elements AE and the measuring probe MP. By pulling the brush through the hair, a friction force in load cell Y (LC-Y) and a bending force in load cell X (LC-X) is induced.

The embodiments of FIGS. 12B-12E are aimed at increasing the amount of hairs that is caught in the system, so as to obtain a stronger measurement signal.

Figure 12B:
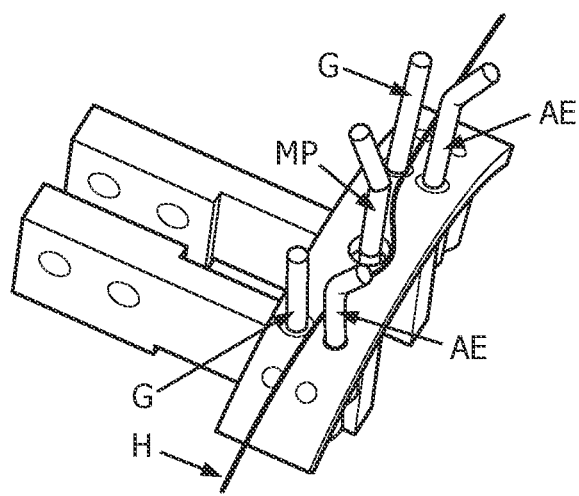

The embodiment of FIG. 12B is an improved version of the execution of FIG. 12A. The tops of the alignment element AE and the measuring probe MP are bent in such a way, that when brushing the hair, more hair is caught in the opening of the measurement system, resulting in a larger measurement signal. An additional guiding pin G is added to reduce dependency on the hold angle of the device.

Figure 12C:
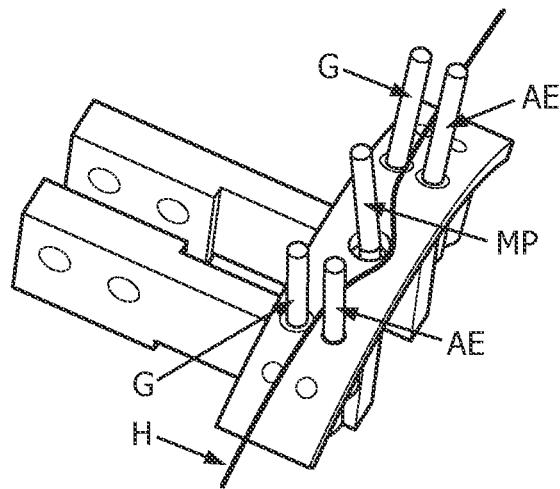

In the embodiment of FIG. 12C, the entire measuring probe MP is put at a small angle. Because of the smaller angle, the hair is caught and kept in the system, as only small forces are needed to do so. As a consequence, the bending force is no longer constant over the length of the measuring system. Because the friction coefficient is the used parameter, tests showed the system is not influenced by the skewness.

Figure 12D:
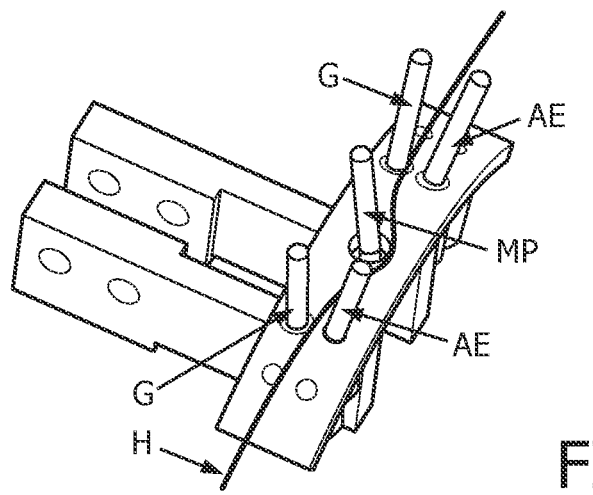

In the embodiment of FIG. 12D, not only the measuring probe MP is at an angle, but also the alignment elements AE. Thereby, even more hair is captured in the system, resulting in a larger measurement signal.

Figure 12E:
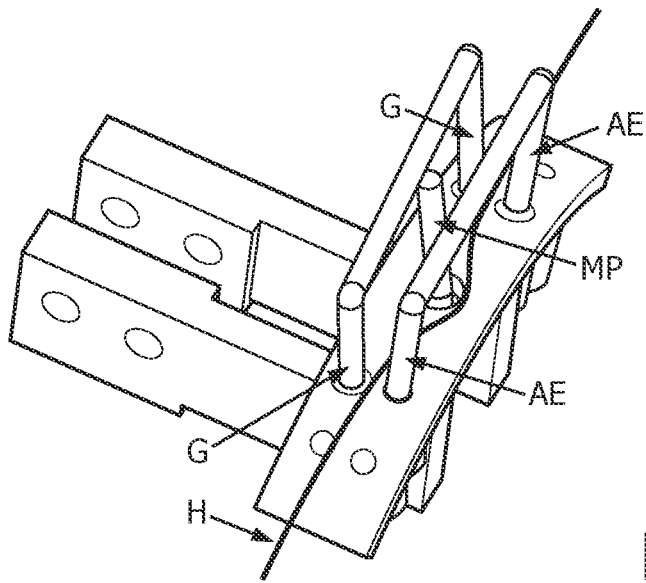

The embodiment of FIG. 12E addresses the issue that when the brush is not put perpendicular to the hair direction on the head, but at a certain angle, hair is guided on the wrong side of the measuring probe MP, resulting in a false measurement signal. To prevent hairs from ending up at the wrong side of the measuring probe MP, both alignment elements AE and both guidance elements G are interlinked. Now hairs will only face the intended side of the measuring probe MP.

It should be noted that the above-mentioned embodiments illustrate rather than limit the invention, and that those skilled in the art will be able to design many alternative embodiments without departing from the scope of the appended claims. In the embodiment of FIG. 7, the dimensions of the measuring probe radius, deflection D and support span SS may size with the area of the measuring probe surface that contacts the hair H. The guidance elements G may be positioned closer to the alignment elements AE rather than at the outer boundaries of the measuring device. The guiding of the hair can be done by a single body containing two guiding features, but it can also be done by two separate guiding features. The spacer can also be placed in another area of the construction in case it is an execution with a hinge. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention may be implemented by means of hardware comprising several distinct elements, and/or by means of a suitably programmed processor to analyze the signal from the measuring probe MP. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A device for measuring properties of hair, the device comprising:
   a first part comprising a measuring probe, and
   a second part arranged for bending the hair against the measuring probe while the hair is guided between the first part and the second part, along the measuring probe, wherein the measuring probe experiences both a friction force resulting from the hair being guided along the measuring probe, and a deformation force resulting from the hair being bent by the second part against the measuring probe, when the device moves through the hair.

2. The device as claimed in claim 1, wherein the measuring probe is movable to allow hair to enter the device.

3. The device as claimed in claim 1, wherein the second part comprises a pressure element arranged for pressing the hair against the measuring probe, the device being arranged for squeezing the hair by the pressure element pushing into the direction of the measuring probe while the hair is being guided between the pressure element and the measuring probe, while the device is arranged for not squeezing the hair before the hair is being guided between the pressure element and the measuring probe.

4. The device as claimed in claim 3, wherein one of the pressure element and the measuring probe comprises a pin, while another one of the pressure element and the measuring probe is provided with a hole for receiving the pin.

5. The device as claimed in claim 1, wherein a spacer is applied between the first part and the second part so as to provide a minimum gap between the measuring probe and the pressure element.

6. The device as claimed in claim 5, wherein the minimum gap has a width of about 0.2 mm.

7. The device as claimed in claim 1, wherein the measuring probe is mounted to a load cell module arranged for measuring a load in two dimensions to measure the friction force and the deformation force, respectively.

8. The device as claimed in claim 1, further comprising an arrangement arranged to compensate for a weight of the measuring probe.

9. The device as claimed in claim 1, wherein the measuring probe is at least partially flexible or tilted.

10. The device as claimed in claim 1, wherein an element of the second part is at least partially flexible or tilted.

11. The device as claimed in claim 1, further comprising a part arranged for preventing the hair from leaving the device in a direction perpendicular to the hair.

12. A device for measuring properties of hair, the device comprising:
a first part comprising a measuring probe, and
a second part arranged for bending the hair against the measuring probe while the hair is guided between the first part and the second part, along the measuring probe, wherein the second part comprises alignment elements at opposite sides of the measuring probe in a plane parallel to a boundary between the first part and the second part for bending the hair against the measuring probe.

13. The device as claimed in claim 12, further comprising guidance elements arranged for mitigating an influence of an angle at which the device is applied to the hair to the friction force or the deformation force.

14. The device as claimed in claim 13, wherein the alignment elements are coupled to each other, and the guidance elements are coupled to each other.

15. The device as claimed in claim 12, further comprising an arrangement arranged to compensate for a weight of the measuring probe.

16. A device for measuring properties of hair, the device comprising:
a first part comprising a measuring probe, a second part arranged for bending the hair against the measuring probe while the hair is guided between the first part and the second part, along the measuring probe, further comprising an accelerometer configured to measure gravity in a measurement direction of the measuring probe.

17. The device as claimed in claim 16, wherein the accelerometer and a sensor that is configured to measure a deformation force are mounted to a same structure in the measuring device.

18. A device for measuring properties of hair, the device comprising:
a first part comprising a measuring probe,
a second part arranged for bending the hair against the measuring probe while the hair is guided between the first part and the second part, along the measuring probe, wherein the device is embedded in a brush having a plurality of bristles.

19. The device as claimed in claim 18, further comprising a treatment plate, wherein the measuring probe is positioned along the treatment plate.

20. The device as claimed in claim 19, wherein a length of the measuring probe substantially matches a length of the treatment plate.

21. The device as claimed in claim 18, further comprising an arrangement arranged to compensate for a weight of the measuring probe.

* * * * *